United States Patent [19]

Avalle

[11] Patent Number: 5,928,655
[45] Date of Patent: Jul. 27, 1999

[54] COMPACT SOLID GEL CONTAINING WATER

[75] Inventor: Nadia Avalle, Milan, Italy

[73] Assignee: Intercos Italia S.p.A., Milan, Italy

[21] Appl. No.: 08/837,821

[22] Filed: Apr. 22, 1997

[30] Foreign Application Priority Data

Apr. 23, 1996 [IT] Italy .................................. MI96A0792

[51] Int. Cl.$^6$ .............................. A61K 7/00; A61K 7/021
[52] U.S. Cl. ......................... 424/401; 424/484; 514/769; 514/770; 514/772.3; 514/777; 514/778; 514/779; 514/782; 514/784; 514/844; 514/944
[58] Field of Search ..................................... 424/484, 485, 424/488, 401; 514/769, 770, 772.3, 778, 777, 779, 784, 782, 844, 944

[56] References Cited

U.S. PATENT DOCUMENTS

| | | | |
|---|---|---|---|
| 3,935,307 | 1/1976 | Aimoto et al. ............................. | 424/49 |
| 4,291,025 | 9/1981 | Pellico ..................................... | 424/180 |
| 4,618,491 | 10/1986 | Kanematu et al. ....................... | 424/81 |
| 4,958,626 | 9/1990 | Nambu et al. ......................... | 128/24 A |

FOREIGN PATENT DOCUMENTS

| | | |
|---|---|---|
| 0 355 908 | 2/1990 | European Pat. Off. . |
| 60-224609 | 11/1985 | Japan . |
| 97-255881 | 3/1997 | Japan . |

*Primary Examiner*—Thurman K. Page
*Assistant Examiner*—James M. Spear
*Attorney, Agent, or Firm*—Jacobson, Price, Holman & Stern, PLLC

[57] ABSTRACT

A compact solid gel is described containing water, that consists of water in a concentration ranging from 15% to 90%, thermoreversible polysaccharides in a concentration ranging from 0.3% to 4%, humectant compounds in a concentration ranging from 4% to 40%, and powder phase in a concentration ranging from 2% to 35%.

11 Claims, No Drawings

COMPACT SOLID GEL CONTAINING WATER

The present invention relates to a compact-structure solid gel containing water.

BACKGROUND OF THE INVENTION

There exist currently on the market several types of gel containing water, both in the sectors of detergency, skin care, sun-cream and in the sectors of make-up products.

These gels have the disadvantage of being in a liquid, semiliquid or pasty form so that it is indispensable for them to be included permanently in a container for confining and containing them, while their use in the form of a stick is substantially prevented.

SUMMARY OF THE INVENTION

The object of the present invention has been that of providing a gel containing water, that exhibits particular features of solidity and compactness, so that it can be applied directly to the skin or taken with the fingers or with a special applicator, in any case without its form having to be compulsorily confined by a container during the application step.

According to the invention such object has been attained with a gel characterized in that it contains the following ingredients:

a) water in a concentration ranging from 15% to 90%;

b) thermoreversible polysaccharides in a concentration ranging from 0.3% to 4%;

c) humectant compounds in a concentration ranging from 4% to 40%;

d) powder phase in a concentration ranging from 2% to 35%.

DESCRIPTION OF PREFERRED EMBODIMENTS

The features of the gel according to the invention are linked to the thermoreversibility of the natural polysaccharide structures singly or in combination with one another, such as Carrageenin, Agar, gellan, alginic acid and salts thereof with alkaline and alkaline-earth metals, in the presence of water either singly or in mixture with humectant substances, in turn either pure or mixed with one another, such as glycerine, polypropylene glycol, hexylene glycol, butylene glycol, pentylene glycol, dipropylene glycol, sorbitol, mannitol, xylitol, PEG POE derivatives, dimethicone copoliol.

Thanks to the thermoreversibility of the polysaccharides, liquid when hot and solid when cold, the product is prepared under heat and then cast in a special die or container, where cooling at room temperature determines a progressive change in the cross-linking of the gel and its consequent solidification with no sharp transition from liquid to solid.

The structure can also be stiffened with electrolytes in a concentration ranging from 0% to 2.5% containing Na+, K+, Ca++, Mg++ cations and Cl-, SO4--, CO3--, PO4--- anions.

The structure of the product can also be modulated with the use of soaps of fatty acids (with chain from C5 to C22) or of soaps of esters of fatty acids (with chain from C5 to C22) with hydroxy acids such as lactic acid, tartaric acid, malic acid, citric acid, succinic acid, in a concentration ranging from 0% to 7%.

The powder phase consists of various excipients of traditional use in cosmetics such as mica, kaolin, talc, nylon 12, starch, zinc oxide, polymers and copolymers of acrylates, of polyethylene, silica, spherical silicas, spherical silicones, singly and in mixture with one another or combined with pigments such as iron oxides, chromium oxides and hydroxides, ultramarine blue, ultramarine rose, manganese violet, titanium dioxide, pearls based on mica and titanium dioxide, pearls based on mica and bismuth oxychloride, carmine, lacquers based on organic dyes as per CTFA.

With the object of improving the dispersion of the pigments in the gel and their correct application on the skin the components of the powder phase are coated singly or in a mixture with silicone, dimethicone, lecithin, perfluoropolyethers, metallic soaps, lauroyl lysine, amino acids.

Excipients coated with one of the materials mentioned above can be mixed with one another in the product.

There is thus obtained a solid, compact product that is easy to spread, that can contain pigments for a decorative application or be a vehicle of active substances and/or sun cream filters.

Thanks to its content of water the gel according to the invention provides at the moment of application a feeling of freshness and forms a film that enhances the life of the pigments and of the vehicle products on the skin.

Moreover, such compact gel allows a more-easily controlled withdrawal that makes the application particularly pleasant. The quantities withdrawn and the thin film of product released on the skin do not provide a feeling of stickiness and the application is homogeneous and well-controlled.

Lastly the short time required for the evaporation of the volatile phase allows a good shading, that gives rise to a film with a good holding ability.

Some formulations suitable for specific destinations of the gel according to the invention are provided hereunder as a non-limiting example.

| SOLID GEL SUN-CREAM | |
|---|---|
| Water | 57.18 |
| Mica | 9.00 |
| Micro titanium dioxide | 8.10 |
| Polysaccharide | 5.00 |
| Hexylene glycol | 5.00 |
| Glycerine | 4.50 |
| Dimethicone Copoliol | 4.50 |
| PEG 200 | 3.20 |
| Fragrance | 0.70 |
| Xanthane gum | 1.00 |
| Phenoxyethanol | 0.30 |
| Methyl parabene | 0.20 |
| Lauroyl lysine | 0.20 |
| Propyl parabene | 0.10 |
| Carrageenin | 1.10 |
| Sodium hyaluronate | 0.02 |
| TOTAL | 100.00 |
| SOLID GEL | |
| Water | 61.15 |
| Biosaccharide Gum-1 | 2.50 |
| Hexylene glycol | 5.00 |
| Glycerine | 4.50 |
| Dimethicone Copoliol | 4.50 |
| PEG 200 | 3.20 |
| Sodium stearate | 1.30 |
| Sodium polymethacrylate | 2.00 |

-continued

| | |
|---|---|
| Sodium chloride | 0.50 |
| Xanthane gum | 1.00 |
| Phenoxyethanol | 0.30 |
| Methyl parabene | 0.25 |
| Lauroyl lysine | 0.20 |
| Propyl parabene | 0.10 |
| Carrageenin | 0.60 |
| Titanium dioxide 77891 | 3.04 |
| Brown iron oxide 77491/92/99 | 1.72 |
| Iron oxide 77492 | 0.14 |
| Iron oxide 77491 | 1.00 |
| Iron oxide 77499 | 1.00 |
| Timica gold bronze | 3.00 |
| Timica brill. gold | 3.00 |
| TOTAL | 100.00 |

SOLID GEL FOR MAKE-UP

| | |
|---|---|
| Water | 55.32 |
| Biosaccharide Gum-1 | 4.00 |
| Glycerine | 1.00 |
| PEG 200 | 16.00 |
| PEG 400 | 3.00 |
| Sodium polymethacrylate | 0.80 |
| Sodium chloride | 1.90 |
| Phenoxyethanol | 0.30 |
| Methyl parabene | 0.25 |
| Sodium stearate | 2.00 |
| Panthenol | 1.00 |
| Propyl parabene | 0.10 |
| Carrageenin | 1.70 |
| Sodium hyaluronate | 0.04 |
| Titanium dioxide 77891 | 8.00 |
| Brown iron oxide 77491/92/99 | 1.20 |
| Iron oxide 77492 | 0.09 |
| Mica | 3.50 |
| TOTAL | 100.00 |

I claim:

1. A compact solid cosmetic gel, particularly for make-up products, consisting of:
   a) water in a concentration ranging from 15% to 90%;
   b) thermoreversible polysaccharides in a concentration ranging from 0.3% to 4%;
   c) humectant compounds in a concentration ranging from 4% to 40%; and
   d) a cosmetically acceptable powder phase in a concentration ranging from 2% to 35%.

2. The gel according to claim 1, wherein said polysaccharides are selected from the group consisting of, singly or in combination, Carrageenin, Agar, gellan, alginic acid and salts thereof with alkaline and alkaline-earth metals.

3. The gel according to claim 1, wherein said humectant compounds are selected from the group consisting of, singly or in combination, glycerine, polypropylene glycol, hexylene glycol, butylene glycol, pentylene glycol, dipropylene glycol, sorbitol, mannitol, xylitol, dimemethicone copoloil.

4. A compact solid cosmetic gel, particularly for make-up products, consisting of:
   a) water in a concentration ranging from 15% to 90%;
   b) thermoreversible polysaccharides in a concentration ranging from 0.3% to 4%;
   c) humectant compounds in a concentration ranging from 4% to 40%;
   d) a cosmetically acceptable powder phase in a concentration ranging from 2% to 35%; and
   e) further comprising electrolytes in a concentration ranging from 0% to 2.5%.

5. A compact solid cosmetic gel, particularly for make-up products, consisting of:
   a) water in a concentration ranging from 15% to 90%;
   b) thermoreversible polysaccharides in a concentration ranging from 0.3% to 4%;
   c) humectant compounds in a concentration ranging from 4% to 40%;
   d) a cosmetically acceptable powder phase in a concentration ranging from 2% to 35%;
   e) electrolytes in a concentration ranging from 0% to 2.5% containing $Na+$, $K+$, $Ca^{2+}$, $Mg^{2+}$ cations and $Cl-$, $SO_4^{2-}$, $CO_3^{2-}$, $PO_4^{3-}$ anions.

6. A compact solid cosmetic gel, particularly for make-up products, consisting of:
   a) water in a concentration ranging from 15% to 90%;
   b) thermoreversible polysaccharides in a concentration ranging from 0.3% to 4%;
   c) humectant compounds in a concentration ranging from 4% to 40%;
   d) a cosmetically acceptable powder phase in a concentration ranging from 2% to 35%; and
   e) soaps of fatty acids having between 5–22 carbon atoms in the chain or soaps of esters of fatty acids having between 5–22 carbon atoms in the chain with hydroxy acids, in a concentration ranging from 0% to 7%.

7. The gel according to claim 1, wherein said powder phase consists of excipients for use in cosmetics, singly or in mixture with one another or combined with pigments.

8. The gel according to claim 1, wherein the components of the powder phase are coated singly or in a mixture with silicone, dimethicone, lecithin, perfluoropolyethers, metallic soaps, lauroyl lysine and amino acids.

9. The gel according to claim 6, wherein said hydroxy acids are selected from the group consisting of lactic acid, tartaric acid, malic acid and succinic acid.

10. The gel according to claim 7 wherein said excipients are selected from the group consisting of mica, kaolin, talc, nylon 12, starch, zinc oxide, polymers and copolymers of acrylates, of polyethylene, silica, spherical silicas and spherical silicones.

11. The gel according to claim 7 wherein said pigments are selected from the group consisting of iron oxides, chromium oxides and hydroxides, ultramarine blue, ultramarine rose, manganese violet, titanium dioxide, pearls based on mica and titanium dioxide pearls based on mica and bysmuth oxy chloride, carmine, lacquers based on organic dyes as per CTFA.

* * * * *